United States Patent

Eller et al.

Patent Number: 5,886,226
Date of Patent: Mar. 23, 1999

[54] PROCESS FOR PRODUCING AMINES FROM OLEFINS ON ZEOLITES OF TYPES SSZ-33, CIT-1 OR MIXTURES THEREOF

[75] Inventors: Karsten Eller, Ludwigshafen; Rudolf Kummer, Frankenthal; Peter Stops, Altrip, all of Germany

[73] Assignee: BASF Aktiengesellschaft, Ludwigshafen, Germany

[21] Appl. No.: 406

[22] PCT Filed: Dec. 4, 1996

[86] PCT No.: PCT/EP96/05406

§ 371 Date: Jan. 29, 1998

§ 102(e) Date: Jan. 29, 1998

[87] PCT Pub. No.: WO97/21661

PCT Pub. Date: Jun. 19, 1997

[30] Foreign Application Priority Data

Dec. 8, 1995 [DE] Germany ............ 19545875.3

[51] Int. Cl.⁶ ................................. C07C 209/60
[52] U.S. Cl. ............................................ 564/485
[58] Field of Search ............................. 564/485

[56] References Cited

U.S. PATENT DOCUMENTS

| | | |
|---|---|---|
| 4,375,002 | 2/1983 | Peterson et al. . |
| 4,536,602 | 8/1985 | Deeba . |
| 4,929,758 | 5/1990 | Taglieber et al. . |

FOREIGN PATENT DOCUMENTS

| | | |
|---|---|---|
| 2092964 | 6/1994 | Canada . |
| 101 921 | 3/1984 | European Pat. Off. . |
| 132 736 | 2/1985 | European Pat. Off. . |
| 133 938 | 3/1985 | European Pat. Off. . |
| 305 564 | 3/1989 | European Pat. Off. . |
| 431 451 | 6/1991 | European Pat. Off. . |
| 42 06 992 | 9/1993 | Germany . |

OTHER PUBLICATIONS

J. Molecular Catalysis, 49 (1989) 235–259.

*Primary Examiner*—Brian M. Burn
*Attorney, Agent, or Firm*—Keil & Weinkauf

[57] ABSTRACT

A process for preparing amines of the general formula I

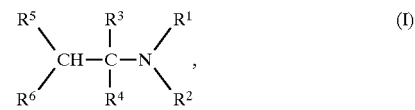

where $R^1$, $R^2$, $R^3$, $R^4$, $R^5$ and $R^6$ are each hydrogen, $C_1$–$C_{20}$-alkyl, $C_2$–$C_{20}$-alkenyl, $C_2$–$C_{20}$-alkynyl, $C_3$–$C_{20}$-cycloalkyl, $C_4$–$C_{20}$-alkylcycloalkyl, $C_4$–$C_{20}$-cycloalkylalkyl, aryl, $C_7$–$C_{20}$-alkylaryl or $C_7$–$C_{20}$-aralkyl, $R^1$ and $R^2$ are together a saturated or unsaturated $C_3$–$C_9$-alkylene dichain, and $R^3$ or $R^5$ are each $C_{21}$–$C_{200}$-alkyl or $C_{21}$–$C_{200}$-alkenyl or together a $C_2$–$C_{12}$-alkylene dichain by reacting olefins of the general formula II

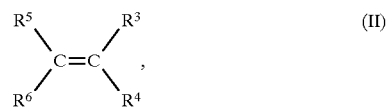

where $R^3$, $R^4$, $R^5$ and $R^6$ are each as defined above, with ammonia or primary or secondary amines of the general formula III

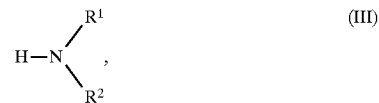

where $R^1$ and $R^2$ are each as defined above, at temperatures from 200° to 350° C. and pressures from 100 to 300 bar in the presence of a heterogeneous catalyst, comprises using a heterogeneous catalyst comprising zeolites of the type SSZ-26, SSZ-33, CIT-1 or mixtures thereof.

11 Claims, No Drawings

PROCESS FOR PRODUCING AMINES FROM OLEFINS ON ZEOLITES OF TYPES SSZ-33, CIT-1 OR MIXTURES THEREOF

The present invention relates to a process for preparing amines by reacting ammonia or primary or secondary amines with olefins at elevated temperatures and pressures in the presence of zeolites of the type SSZ-26, SSZ-33, CIT-1 or mixtures thereof.

Methods for aminating olefins are reviewed in Functionalisation of Alkenes: Catalytic Amination of Monoolefins, J. J. Brunet et al. J. Mol. Catal., 49 (1989), 235–259.

There are basically two mechanisms of catalysis. The olefin is coordinated by a metal complex. This activated species can be attacked by nucleophilic amines to form a more highly aminated product. The amine can be chemisorbed on acid centers or on metal centers (via metal amides) and reacted with the olefin in this activated state.

Zeolites are very useful catalysts. They have a large number of catalytically active centers combined with a large surface area. The zeolites which have been described differ in type and in the aftertreatment (eg. thermal treatment, dealumination, acid treatment, metal ion exchange, etc.). Examples may be found in U.S. Pat. No. 4,375,002, U.S. Pat. No. 4,536,602, EP-A-305 564, EP-A-101 921, DE-A-42 06 992.

EP-A-133 938, EP-A-431 451 and EP-A-132 736 disclose processes wherein borosilicate, gallium silicate, aluminosilicate and iron silicate zeolites are used for preparing amines from olefins and mention the possibility of doping these zeolites with alkali, alkaline earth and transition metals.

CA-A-2 092 964 discloses a process for preparing amines from olefins using BETA zeolites, which are defined as crystalline aluminosilicates of a certain composition with a pore size of greater than 5 Å. Preference is given to using metal- or halogen-modified beta zeolites.

All processes for synthesizing amines from olefins over these catalysts have a low amine yield or a low space-time yield or lead to a rapid deactivation of the catalysts.

It is an object of the present invention to overcome these disadvantages.

We have found that this object is achieved by a novel and improved process for preparing amines of the general formula I

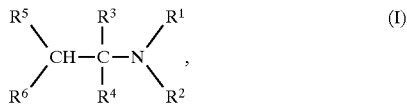

where $R^1$, $R^2$, $R^3$, $R^4$, $R^5$ and $R^6$ are each hydrogen, $C_1$–$C_{20}$-alkyl, $C_2$–$C_{20}$-alkenyl, $C_2$–$C_{20}$-alkynyl, $C_3$–$C_{20}$-cycloalkyl, $C_4$–$C_{20}$-alkylcycloalkyl, $C_4$–$C_{20}$-cycloalkylalkyl, aryl, $C_7$–$C_{20}$-alkylaryl or $C_7$–$C_{20}$-aralkyl, $R^1$ and $R^2$ are together a saturated or unsaturated $C_3$–$C_9$-alkylene dichain, and $R^3$ or $R^5$ are each $C_{21}$–$C_{200}$-alkyl or $C_{21}$–$C_{200}$-alkenyl or together a $C_2$–$C_{12}$-alkylene dichain by reacting olefins of the general formula II

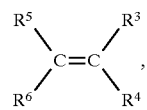

where $R^3$, $R^4$, $R^5$ and $R^6$ are each as defined above, with ammonia or primary or secondary amines of the general formula III

where $R^1$ and $R^2$ are each as defined above, at temperatures from 200° to 350° C. and pressures from 100 to 300 bar in the presence of a heterogeneous catalyst, which comprises using a heterogeneous catalyst comprising zeolites of the type SSZ-26, SSZ-33, CIT-1 or mixtures thereof.

The process of the present invention can be carried out as follows:

The olefin II and ammonia or the primary or secondary amine III can be reacted at temperatures from 200° to 350° C., preferably from 220° to 330° C., particularly preferably from 230° to 320° C., and pressures from 100 to 300 bar, preferably from 120 to 300 bar, particularly preferably from 140 to 290 bar, in the presence of zeolites of the type SSZ-26, SSZ-33, CIT-1 or mixtures thereof as catalysts, for example in a pressure reactor, and preferably the amine obtained is separated off and the unconverted feed materials are recycled.

The present process gives a very good yield combined with a high selectivity and a high space-time yield. In addition, the deactivation of the catalyst has been suppressed.

Even with a small excess of ammonia or amine, the process of the present invention achieves a high selectivity to desired reaction product and dimerization and/or oligomerization of the olefin used is avoided.

In one embodiment of this process, ammonia and/or amines III are fed together with the olefin II in a mixture in a molar ratio of from 1:1 to 5:1 into a fixed-bed reactor and reacted therein at a pressure of from 100 to 300 bar and a temperature of from 200° to 350° C. in the gas phase or in the supercritical state.

The desired product can be obtained from the reaction effluent by means of known methods, for example distillation or extraction, and if necessary brought to the desired purity by means of further separating operations. Preference is generally given to recycling the unconverted feed materials into the reactor.

It is possible to use monounsaturated or polyunsaturated olefins II, in particular those having 2 to 10 carbon atoms, or mixtures thereof and polyolefins as starting materials. Owing to the less pronounced tendency to polymerize, monoolefins are more suitable than di- and polyolefins, but the latter can be reacted just as selectively by means of higher ammonia or amine excesses. The position of the equilibrium and hence the conversion to the desired amine is very highly dependent on the reaction pressure used. High pressure favors the addition product, but the pressure range of up to 300 bar will generally represent the optimum for technical and commercial reasons. The selectivity of the reaction is influenced not only by variables such as ammonia/amine excess and catalyst but also to a high degree by the temperature. Although the reaction rate of the addition reaction increases strongly with increasing temperature, competing cracking and recombination reactions of the olefin are promoted at the same time. In addition, a temperature increase is not advantageous from a thermodynamic point of view. The position of the temperature optimum as regards conversion and selectivity is dependent on the constitution of the olefin, of the amine used and of the catalyst and is usually within the range from 200° to 350° C.

Suitable catalysts for the amination of olefins are zeolites of the type SSZ-26, SSZ-33, CIT-1 or mixtures thereof. The preparation of SSZ-26 is described in U.S. Pat. No. 4,910,006, the preparation of SSZ-33 is described in U.S. Pat. No. 4,963,337, U.S. Pat. No. 5,120,425 and WO-A-94/00233 and the preparation of CIT-1 is described in WO-A-95/07859. It is known from Stud. Surf. Sci. Catal., 84, 461 to 468 (1994), that the aluminosilicate SSZ-26 and the two borosilicates SSZ-33 and CIT-1 have very closely related structures and differ only in the stacking sequence of two different polymorphs.

The zeolites SSZ-26, SSZ-33 and CIT-1 of the present invention can be molded as such or else using a binder in a ratio of from 98:2 to 40:60% by weight into extrudates or tablets. Suitable binders include various aluminas, preferably boehmite, amorphous aluminosilicates having an $SiO_2/Al_2O_3$ ratio of from 25:75 to 95:5, silica, preferably finely divided $SiO_2$, mixtures of finely divided $SiO_2$ and finely divided $Al_2O_3$, finely divided $TiO_2$, and clays. After molding, the extrudates or tablets are advantageously dried at 110° C. for 16 h and calcined at from 200° to 500° C. for from 2 to 16 h and the calcination can also take place directly in the amination reactor.

The zeolite catalysts SSZ-26, SSZ-33 and CIT-1 of the present invention may be modified in various ways in order to increase the selectivity, the on-stream time and the number of possible regenerations.

One way of modifying the catalysts comprises ion-exchanging or doping the molded or unmolded zeolites with alkali metals such as Na and K, alkaline earth metals such as Ca and Mg, earth metals such as Tl, transition metals such as, for example, Ti, Zr, Mn, Fe, Mo, Cu, Zn, Cr, noble metals and/or rare earth metals such as, for example, La, Ce or Y.

In an advantageous embodiment the molded zeolites SSZ-26, SSZ-33 and CIT-1 of the present invention are placed in a flow tube and, for example, a halide, an acetate, an oxalate, a citrate or a nitrate of the above-described metals in dissolved form is passed over at from 20° to 100° C. Such an ion exchange can be carried out, for example, on the hydrogen, ammonium or alkali metal form of the zeolites SSZ-26, SSZ-33 and CIT-1 of the present invention.

A further way of applying metal to the zeolites SSZ-26, SSZ-33 and CIT-1 of the present invention comprises impregnating the material, for example with a halide, an acetate, an oxalate, a citrate, a nitrate or an oxide of the above-described metals in aqueous or alcoholic solution.

Both ion exchange and impregnation may be followed by drying, and, if desired, further calcination. In the case of metal-doped zeolites of the type SSZ-26, SSZ-33 and CIT-1, aftertreatment with hydrogen and/or with steam may be advantageous.

Another possible method of modification involves subjecting the molded or unmolded zeolites SSZ-26, SSZ-33 and CIT-1 of the present invention to a treatment with acids, such as hydrochloric acid (HCl), hydrofluoric acid (HF), sulfuric acid ($H_2SO_4$), oxalic acid ($HO_2C$—$CO_2H$), phosphoric acid ($H_3PO_4$) or mixtures thereof.

A particular embodiment comprises refluxing the zeolites SSZ-26, SSZ-33 and CIT-1 of the present invention for from 1 to 100 hours with one of the aforementioned acids at from 0.001N to 2N, preferably from 0.05 to 0.5N, prior to molding. Collection by filtration and washing are generally followed by drying at from 100° to 160° C. and calcining at from 200° to 600° C. A further particular embodiment comprises an acid treatment of the zeolites SSZ-26, SSZ-33 and CIT-1 of the present invention after their molding with binder. The zeolite of the present invention is generally treated for from 1 to 3 hours at from 60° to 80° C. with an acid from 3 to 25% in strength, in particular from 12 to 20% in strength, then washed, dried at from 100° to 160° C. and calcined at from 200° to 600° C. Here, too, it is possible for the calcination to be carried out directly in the amination reactor.

Another possible method of modification is by exchange with ammonium salts, for example with $NH_4Cl$, or with mono-, di- or polyamines. The binder-molded zeolite is subjected to exchange continuously for 2 hours at from 60° to 80° C. with from 10 to 25% in strength, preferably 20% in strength, $NH_4Cl$ solution in a solution containing zeolite and ammonium chloride in a weight ratio of 1:15, and then dried at from 100° to 120° C.

A further modification which can be carried out on the zeolites of the present invention is, in the case of the aluminum zeolite SSZ-26, a dealumination wherein some of the aluminum atoms are replaced by silicon or is removed by a hydrothermal treatment, for example. A hydrothermal dealumination is advantageously followed by an extraction with acids or complexing agents to remove non-lattice aluminum formed. The replacement of aluminum by silicon can be effected, for example, with $(NH_4)_2SiF_6$ or $SiCl_4$. Examples of dealuminations of Y zeolites are found in Corma et al., Stud. Surf. Sci. Catal. 37 (1987), 495–503. Correspondingly, in the case of the boron zeolites SSZ-33 and CIT-1, some of the boron can be removed and replaced by silicon.

The catalysts can be used for the amination of olefins in the form of extrudates having diameters of, for example, from 1 to 4 mm, or in the form of tablets having diameters of, for example, from 3 to 5 mm.

A fluidizable material having a size of from 0.1 to 0.8 mm can be obtained from the catalyst, which has been molded into extrudates for example, by milling and sieving.

The substituents $R^1$, $R^2$, $R^3$, $R^4$, $R^5$ and $R^6$ in the compounds I, II and III have the following meanings:

$R^1$, $R^2$, $R^3$, $R^4$, $R^5$, $R^6$ hydrogen, $C_1$–$C_{20}$-alkyl, preferably $C_1$–$C_{12}$-alkyl, particularly preferably $C_1$–$C_8$-alkyl such as methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl and isooctyl, $C_2$–$C_{20}$-alkenyl, preferably $C_2$–$C_{12}$-alkenyl, particularly preferably $C_2$–$C_8$-alkenyl such as vinyl and allyl, $C_2$–$C_{20}$-alkynyl, preferably $C_2$–$C_8$-alkynyl, in particular $C_2H$ and propargyl, $C_3$–$C_{20}$-cycloalkyl, preferably $C_3$–$C_{12}$-cycloalkyl, particularly preferably $C_5$–$C_8$-cycloalkyl such as cyclopentyl, cyclohexyl, cycloheptyl and cyclooctyl, $C_4$–$C_{20}$-alkylcycloalkyl, preferably $C_4$–$C_{12}$-alkylcycloalkyl, particularly preferably $C_5$–$C_{10}$-alkylcycloalkyl, $C_4$–$C_{20}$-cycloalkylalkyl, preferably $C_4$–$C_{12}$-cycloalkylalkyl, particularly preferably $C_5$–$C_{10}$-cycloalkylalkyl, aryl such as phenyl, 1-naphthyl and 2-naphthyl, preferably phenyl, $C_7$–$C_{20}$-alkylaryl, preferably $C_7$–$C_{16}$-alkylaryl, preferably $C_7$-$C_{12}$-alkylphenyl such as 2-methylphenyl, 3-methylphenyl, 4-methylphenyl, 2-ethylphenyl, 3-ethylphenyl and 4-ethylphenyl, $C_7$–$C_{20}$-aralkyl, preferably $C_7$–$C_{16}$-aralkyl, preferably $C_7$–$C_{12}$-phenalkyl such as phenylmethyl, 1-phenylethyl, 2-phenylethyl, $R^1$ and $R^2$ together a saturated or unsaturated $C_3$–$C_9$-alkylene dichain, preferably —$(CH_2)_4$—, —$(CH_2)_5$—, —$(CH_2)_7$— and —CH=CH—CH=CH—, $R^3$ or $R^5$ $C_{21}$–$C_{200}$-alkyl, preferably $C_{40}$–$C_{200}$-alkyl, such polybutyl, polyisobutyl, polypropyl, polyisopropyl and polyethyl, particularly preferably polybutyl and polyisobutyl, $C_{21}$–$C_{200}$-alkenyl, preferably $C_{40}$–$C_{200}$-alkenyl, particularly preferably $C_{70}$–$C_{170}$-alkenyl, $R^3$ and $R^5$ together a $C_2$–$C_{12}$-alkylene dichain, preferably a $C_3$–$C_8$-alkylene dichain, particularly preferably —$(CH_2)_3$—, —$(CH_2)_4$—, —$(CH_2)_5$—, —$(CH_2)_6$— and —$(CH_2)_7$—, in particular —$(CH_2)_3$— and —$(CH_2)_4$—.

EXAMPLES

Catalyst Synthesis

Catalyst A 30 g of SSZ-26 were compacted with 20 g of boehmite and 1 g of formic acid in a kneader and kneaded for 45 minutes with the addition of 65 ml of water. 2 mm extrudates were produced in an extruder under a molding pressure of 40 bar, dried at 120° C. for 16 hours and then calcined at 500° C. for 16 hours.

Catalyst B 30 g of SSZ-33 were compacted with 20 g of boehmite and 1 g of formic acid in a kneader and kneaded for 45 minutes with the addition of 49 ml of water. 2 mm extrudates were produced in an extruder under a molding pressure of 40 bar, dried at 120° C. for 16 hours and then calcined at 500° C. for 16 hours.

Catalyst C 30 g of CIT-1 were compacted with 20 g of boehmite and 1 g of formic acid in a kneader and kneaded for 45 minutes with the addition of 67 ml of water. 2 mm extrudates were produced in an extruder under a molding pressure of 40 bar, dried at 120° C. for 16 hours and then calcined at 500° C. for 16 hours.

Amination Examples

The experiments were carried out in a tubular reactor (6 mm internal diameter) under isothermal conditions at from 260° to 300° C. and a pressure of 280 bar using a mixture of isobutene and ammonia in a molar ratio of 1:1.5. The reaction products were analyzed by gas chromatography. The results are summarized in Table 1.

TABLE 1 tert-Butylamine (NH$_3$: C$_4$H$_8$ = 1.5)

| Catalyst | Pressure [bar] | Temperature [°C.] | tert-Butylamine yields [wt %] | | | Weight per liter [kg/l] |
|---|---|---|---|---|---|---|
| | | | WHSV 0.7 [g/g · h] | WHSV 1.5 [g/g · h] | WHSV 3 [g/g · h] | |
| A | 280 | 260 | 19.2 | | | 0.48 |
| A | 280 | 270 | 20.9 | 18.2 | 14.6 | 0.48 |

TABLE 1-continued tert-Butylamine (NH$_3$: C$_4$H$_8$ = 1.5)

| Catalyst | Pressure [bar] | Temperature [°C.] | tert-Butylamine yields [wt %] | | | Weight per liter [kg/l] |
|---|---|---|---|---|---|---|
| | | | WHSV 0.7 [g/g · h] | WHSV 1.5 [g/g · h] | WHSV 3 [g/g · h] | |
| A | 280 | 280 | 18.0 | 17.5 | 15.2 | 0.48 |
| A | 280 | 300 | | | 12.6 | 0.48 |
| B | 280 | 290 | 17.7 | 17.0 | 13.5 | 0.52 |
| C | 280 | 275 | 19.2 | 18.0 | 15.0 | 0.50 |

We claim:

1. A process for preparing amines of the general formula I

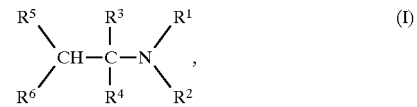

where $R^1$, $R^2$, $R^3$, $R^4$, $R^5$ and $R^6$ are each hydrogen, $C_1$–$C_{20}$-alkyl, $C_2$–$C_{20}$-alkenyl, $C_2$–$C_{20}$-alkynyl, $C_3$–$C_{20}$-cycloalkyl, $C_4$–$C_{20}$-alkylcycloalkyl, $C_4$–$C_{20}$-cycloalkylalkyl, aryl, $C_7$–$C_{20}$-alkylaryl or $C_7$–$C_{20}$-aralkyl, $R^1$ and $R^2$ are together a saturated or unsaturated $C_3$–$C_9$-alkylene dichain, and $R^3$ or $R^5$ are each $C_{21}$–$C_{200}$-alkyl or $C_{21}$–$C_{200}$-alkenyl or together a $C_2$–$C_{12}$-alkylene dichain, by reacting olefins of the general formula II

where $R^3$, $R^4$, $R^5$ and $R^6$ are each as defined above, with ammonia or primary or secondary amines of the general formula III

where $R^1$ and $R^2$ are each as defined above, at temperatures from 200° to 350° C. and pressures from 100 to 300 bar in the presence of a heterogeneous catalyst, which comprises using a heterogeneous catalyst comprising zeolites of the type SSZ-26, SSZ-33, CIT-1 or mixtures thereof.

2. A process for preparing amines I as claimed in claim 1, wherein the product amine I is separated off and the unconverted feed materials II and III are recycled.

3. A process for preparing amines as claimed in claim 1, wherein olefin II is isobutene, diisobutene, cyclopentene, cyclohexene or polyisobutene.

4. A process for preparing amines as claimed in claim 1, wherein the heterogeneous catalyst used comprises a zeolite of the type SSZ-26, SSZ-33, CIT-1 or a mixture thereof in the H-form.

5. A process for preparing amines as claimed in claim 1, wherein the heterogeneous catalyst used comprises a zeolite of the type SSZ-26, SSZ-33, CIT-1 or a mixture thereof which has been treated with an acid, in particular with an acid selected from the group consisting of hydrochloric acid, hydrofluoric acid, sulfuric acid, oxalic acid, phosphoric acid or mixtures thereof.

6. A process for preparing amines as claimed in claim 1, wherein the heterogeneous catalyst used comprises a zeolite of the type SSZ-26, SSZ-33, CIT-1 or a mixture thereof doped with one or more transition metals.

7. A process for preparing amines as claimed in claim 1, wherein the heterogeneous catalyst used comprises a zeolite of the type SSZ-26, SSZ-33, CIT-1 or a mixture thereof doped with one or more rare earth elements.

8. A process for preparing amines as claimed in claim 1, wherein the heterogeneous catalyst used comprises a zeolite of the type SSZ-26, SSZ-33, CIT-1 or a mixture thereof in the ammonium form.

9. A process for preparing amines as claimed in claim 1, wherein the heterogeneous catalyst used comprises a zeolite of the type SSZ-26, SSZ-33, CIT-1 or a mixture thereof doped with one or more elements from the group of the alkali, alkaline earth or earth metals.

10. A process for preparing amines as claimed in claim 1, wherein the heterogeneous catalyst used comprises a zeolite of the type SSZ-26, SSZ-33, CIT-1 or a mixture thereof molded with a binder and calcined at temperatures from 200° to 600° C.

11. A process for preparing amines as claimed in claim 1, wherein the heterogeneous catalyst used comprises a dealuminated or deborated zeolite of the type SSZ-26, SSZ-33, CIT-1 or a mixture thereof.

* * * * *